US010582989B2

(12) United States Patent
Wallace

(10) Patent No.: US 10,582,989 B2
(45) Date of Patent: Mar. 10, 2020

(54) ORAL HYGIENE DEVICE

(71) Applicant: David Barrett Wallace, Salt Lake City, UT (US)

(72) Inventor: David Barrett Wallace, Salt Lake City, UT (US)

( * ) Notice: Subject to any disclaimer, the term of this patent is extended or adjusted under 35 U.S.C. 154(b) by 337 days.

(21) Appl. No.: 15/372,095

(22) Filed: Dec. 7, 2016

(65) Prior Publication Data

US 2017/0156830 A1    Jun. 8, 2017

Related U.S. Application Data

(60) Provisional application No. 62/264,000, filed on Dec. 7, 2015.

(51) Int. Cl.
| | | |
|---|---|---|
| *A61C 15/00* | (2006.01) | |
| *A61C 15/04* | (2006.01) | |
| *A61C 9/00* | (2006.01) | |
| *B33Y 10/00* | (2015.01) | |
| *B33Y 50/00* | (2015.01) | |

(Continued)

(52) U.S. Cl.
CPC .......... *A61C 15/046* (2013.01); *A61C 9/0006* (2013.01); *A61C 2201/002* (2013.01); *B33Y 10/00* (2014.12); *B33Y 50/00* (2014.12); *B33Y 80/00* (2014.12); *B33Y 99/00* (2014.12)

(58) Field of Classification Search
CPC ......... A61C 12/046; A61C 9/00; A61C 15/00; A61C 15/043; A61C 15/045; A61C 9/0006; B33Y 10/00; B33Y 50/00; B33Y 80/00; B33Y 99/00
See application file for complete search history.

(56) References Cited

U.S. PATENT DOCUMENTS 3,311,977 A  *  4/1967  Drake .................... A61C 7/08
                                                 433/6
3,319,626 A  *  5/1967  Lindsay ............... A63B 71/085
                                                 128/861

(Continued)

FOREIGN PATENT DOCUMENTS

WO        2015003681 A1    1/2015

OTHER PUBLICATIONS

International Search Report and Written Opinion dated Feb. 16, 2017 from International Patent Application No. PCT/US2016/065429, filed Dec. 7, 2016.

*Primary Examiner* — Nicholas D Lucchesi
(74) *Attorney, Agent, or Firm* — David B. Tingey; Bryant J. Keller; Kirton McConkie

(57) ABSTRACT

An oral hygiene device is provided. The oral hygiene device includes a body having a base and first and second opposing sides extending from the base and defining a gap therebetween. The device may further include a plurality of corresponding notch pairs, wherein each corresponding notch pair has a first notch positioned in the first opposing side and a second notch positioned in the second opposing side. The location of the notch pairs may coincide with a user's mouth and in particular to the position of the user's teeth within the mouth. As such, a fibrous material, such as floss, may be coupled to the device such that the material spans the gap between at least one of the corresponding notch pairs so that the material may be inserted into the spaces between the user's teeth when the device is placed into the user's mouth.

20 Claims, 9 Drawing Sheets

(51) Int. Cl.
*B33Y 80/00* (2015.01)
*B33Y 99/00* (2015.01)

(56) References Cited

U.S. PATENT DOCUMENTS

| | | | |
|---|---|---|---|
| 3,335,718 A | 8/1967 | Sexton | |
| 4,059,101 A | 11/1977 | Richmond | |
| 4,350,154 A * | 9/1982 | Feldbau | A63B 71/085 |
| | | | 128/861 |
| 4,505,672 A * | 3/1985 | Kurz | A61C 7/08 |
| | | | 433/6 |
| 5,022,417 A * | 6/1991 | Cimini | A61C 15/046 |
| | | | 132/323 |
| 5,190,062 A | 3/1993 | Rafaeli | |
| 5,429,145 A * | 7/1995 | Bral | A61C 15/046 |
| | | | 132/323 |
| 7,904,307 B2 | 3/2011 | Abolfathi et al. | |
| 2003/0044748 A1* | 3/2003 | Tucker | A61C 9/0006 |
| | | | 433/38 |
| 2003/0140937 A1 | 7/2003 | Cook | |
| 2005/0133057 A1 | 6/2005 | Kirstein | |
| 2006/0014121 A1* | 1/2006 | DelGrosso | A61C 15/046 |
| | | | 433/216 |
| 2009/0194133 A1* | 8/2009 | Toor | A61C 15/045 |
| | | | 132/324 |
| 2012/0318289 A1* | 12/2012 | Sahoo | A61C 15/046 |
| | | | 132/200 |
| 2013/0220356 A1* | 8/2013 | Sahoo | A61C 15/042 |
| | | | 132/200 |

* cited by examiner

ORAL HYGIENE DEVICE

CROSS REFERENCE TO RELATED APPLICATION

This application claims priority to U.S. Provisional Patent Application No. 62/264,000 to Wallace, filed Dec. 7, 2015, the disclosure of which is hereby incorporated entirely herein by reference.

BACKGROUND

Technical Field

The present disclosure relates to oral hygiene, and in particular to an oral hygiene device and method of using and making the same.

State of the Art

Proper oral hygiene includes careful and frequent brushing with a toothbrush to help prevent build-up of plaque bacteria on the teeth. In addition to brushing, cleaning between teeth may help to prevent build-up of plaque bacteria. Cleaning between teeth may be done with dental floss or interdental brushes.

However, ranging from the process taking too much time to fingers being too large, the justifications for not flossing one's teeth are numerous, and many persons simply have difficulty with the mechanics of flossing even after learning to do it the right way.

It would therefore be advantageous to address these justifications and provide a new and improved oral hygiene device, including methods of using and manufacturing the same.

SUMMARY

The present disclosure relates to oral hygiene, and in particular to a teeth cleaning device and method of using and making the same.

An aspect of the present disclosure includes an oral hygiene device comprising: a body having a base and opposing sides extending from the base; and a plurality of notches in each of the opposing sides, wherein each notch is positioned to correspond to a user's teeth.

Another aspect of the present disclosure includes an oral hygiene device comprising: a body having a base and first and second opposing sides extending from the base, the first and second opposing sides defining a gap therebetween; a plurality of corresponding notch pairs, wherein each corresponding notch pair has a first notch positioned in the first opposing side and a second notch positioned in the second opposing side; and a fibrous material spanning the gap between at least one of the corresponding notch pairs.

Another aspect of the present disclosure includes a method of cleaning teeth comprising: providing an oral hygiene device having opposing sides defining a gap therebetween; stringing a fibrous material between the opposing sides to span the gap at a plurality of locations; placing the device into a user's mouth; and applying the fibrous material concurrently into spaces defined between the user's teeth.

Another aspect of the present disclosure includes a process of manufacturing an oral hygiene device comprising: making impressions of a user's teeth; creating a model of the user's teeth from the impressions; designing an oral hygiene device from the model; and 3-D printing the device.

Another aspect of the present disclosure includes an oral hygiene device comprising: a body having first and second opposing sides, the first and second opposing sides defining a gap or distance therebetween; a plurality of corresponding notch pairs, wherein each corresponding notch pair has a first notch positioned in the first opposing side and a second notch positioned in the second opposing side; a stability member spanning the distance between the first and second opposing sides at distal ends of the first and second opposing sides; and a material spanning the distance between at least one of the corresponding notch pairs, wherein the material is wound about the body and in the at least one corresponding notch pair, wherein the device is insertable within a user's mouth and each corresponding notch pair is configured to correspond to dental anatomy of the user, wherein corresponding notch pairs are positioned to substantially align with a space between neighboring teeth of the user.

The foregoing and other features, advantages, and construction of the present disclosure will be more readily apparent and fully appreciated from the following more detailed description of the particular embodiments, taken in conjunction with the accompanying drawings.

BRIEF DESCRIPTION OF THE DRAWINGS

Some of the embodiments will be described in detail, with reference to the following figures, wherein like designations denote like members.

DETAILED DESCRIPTION OF EMBODIMENTS

Figure 1:
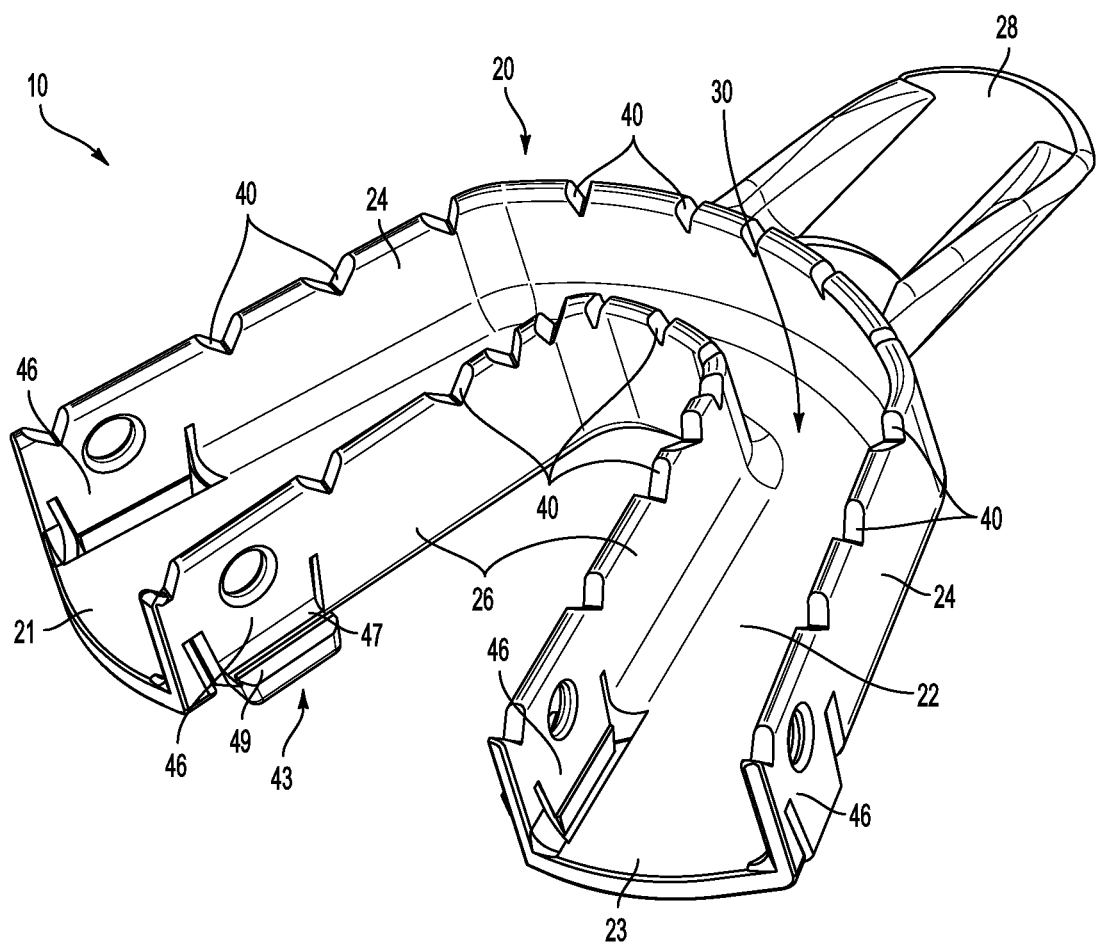
FIG. 1 is a perspective view of an embodiment of an oral hygiene device in accordance with the present disclosure.
Figure 2:
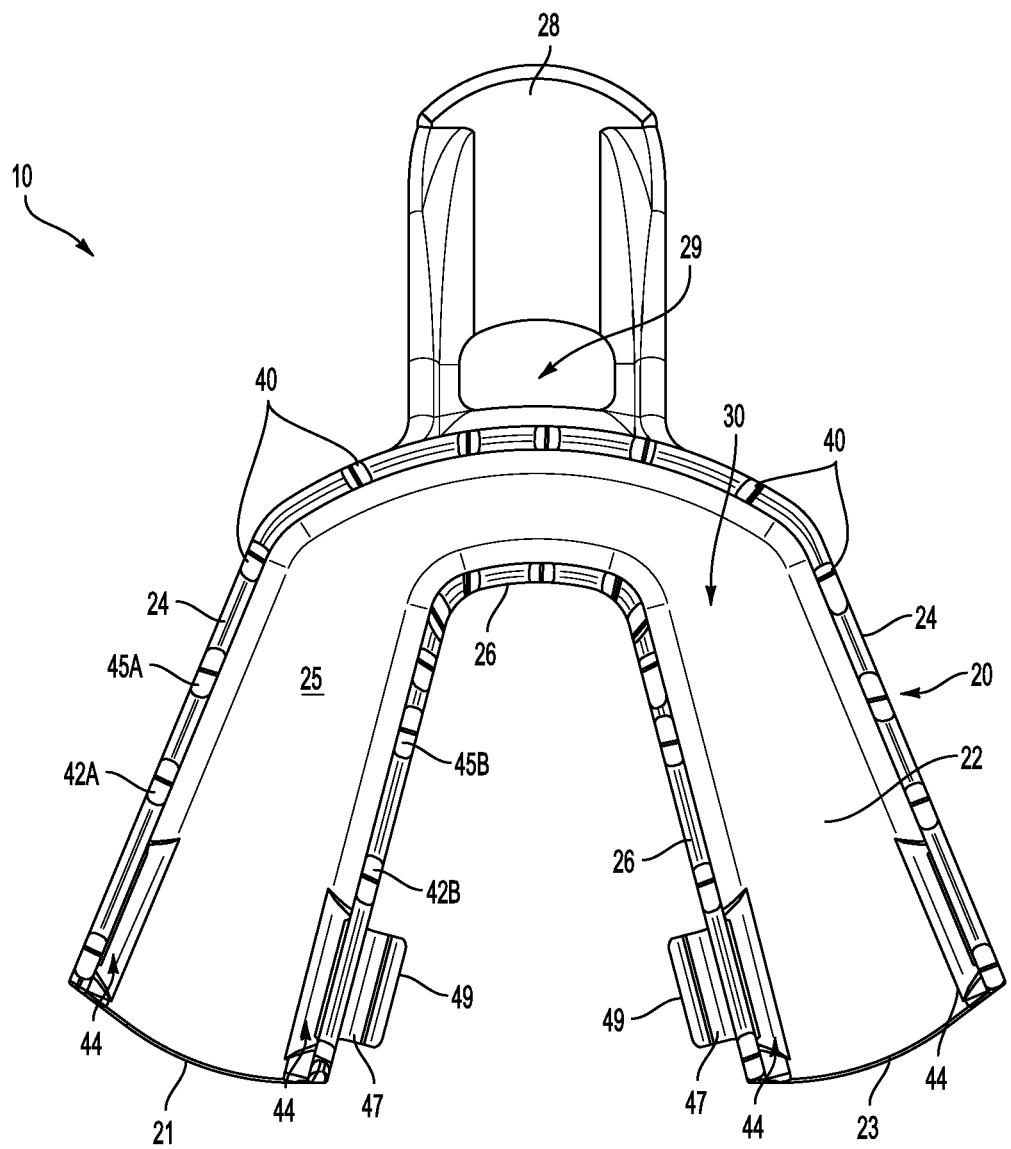
FIG. 2 is a top view of an embodiment of the oral hygiene device in accordance with the present disclosure.
Figure 3:
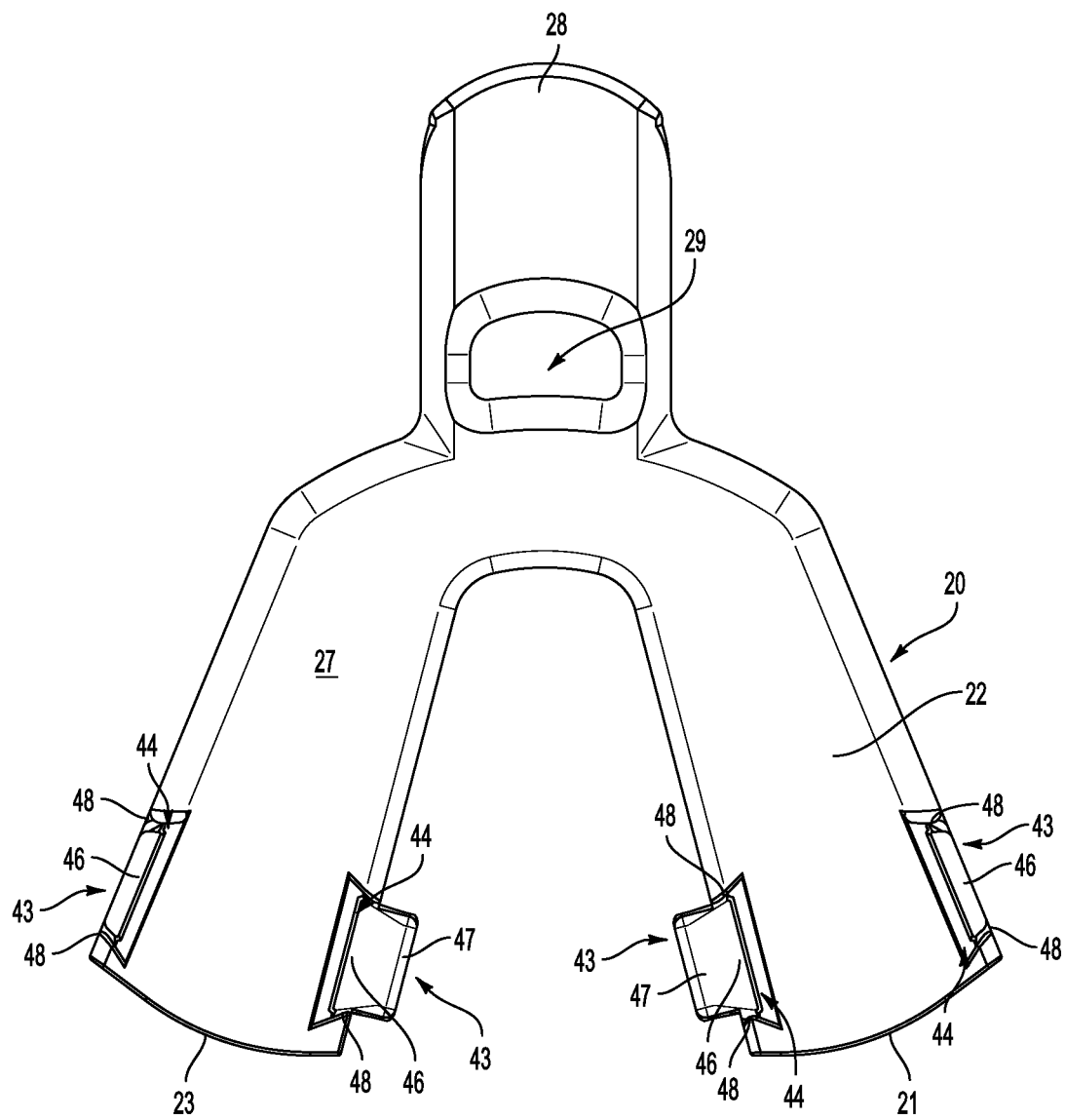
FIG. 3 is a bottom view of an embodiment of the oral hygiene device in accordance with the present disclosure.
Figure 4:
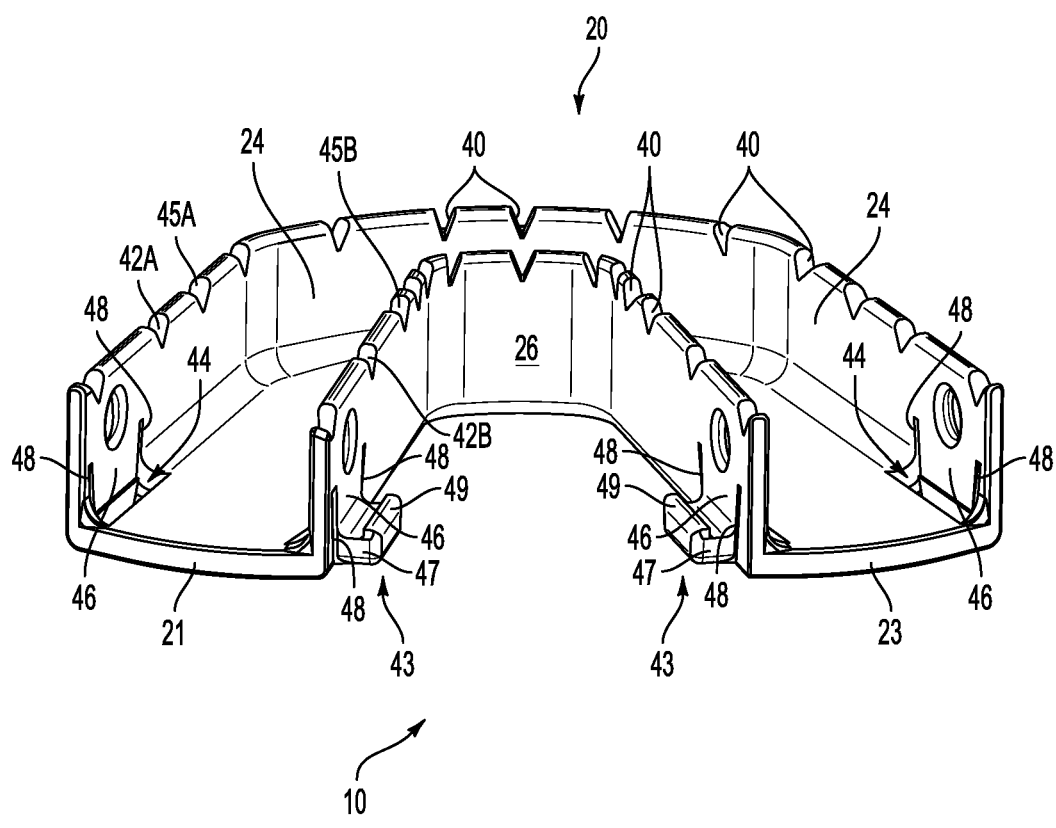
FIG. 4 is a front perspective view of an embodiment of the oral hygiene device in accordance with the present disclosure.

A detailed description of the hereinafter described embodiments of the disclosed apparatus and method are presented herein by way of exemplification and not limitation with reference to the Figures listed above. Although certain embodiments are shown and described in detail, it should be understood that various changes and modifications may be made without departing from the scope of the appended claims. The scope of the present disclosure will in no way be limited to the number of constituting components, the materials thereof, the shapes thereof, the relative arrangement thereof, etc., and are disclosed simply as an example of embodiments of the present disclosure.

As a preface to the detailed description, it should be noted that, as used in this specification and the appended claims, the singular forms "a", "an" and "the" include plural referents, unless the context clearly dictates otherwise.

The drawings depict illustrative embodiments of an oral hygiene device 10. These embodiments may each comprise various structural and functional components that complement one another to provide the unique functionality and performance of the oral hygiene device 10, the particular structure and function of which will be described in greater detail herein.

Referring to the drawings, FIGS. 1-5 depict illustrative embodiments of an oral hygiene device 10. Embodiments of the oral hygiene device 10 may comprise, among other features, a body portion 20, opposing sidewalls 24 and 26, and notches 40.

Embodiments of the oral hygiene device 10 may comprise a body portion 20. The body portion 20 may have a flat, level, even, uniform, or substantially smooth base 22 having a first surface 25 and a second surface 27, the second surface 27 on an opposite side of the first surface 25, or opposing the first surface 25. Alternatively, the base 22 may have a textured surface or non-uniform surface features. The base 22 may have a length between opposing distal ends 21 and 23 and may be formed in an elongate or, alternatively, a semi-circular shape. The base 22 and body portion 20 may also be formed in shapes that are conducive to being placed in an oral cavity, such as a mouth. The base 22 and/or body portion 20 may be shaped or formed to fit the general curvature of a mouth, and in particular a line of teeth within a mouth. The length of the base 22 and/or body portion 20 may be sized and shaped to fit, match, correspond, or otherwise relate to the length of the line of teeth in a mouth. For example, the distal ends 21 and 23 may be rounded and softened so as to not be jagged, sharp, pointy, or otherwise harsh to the user's mouth and/or gums when the device 10 is placed in the user's mouth. Moreover, other edges or ends of the device 10, such as for example, the sidewalls 24 and 26 may also be rounded or softened for the same reasons.

Embodiments of the oral hygiene device 10 may further comprise the body portion 20 having a gripping member 28 extending therefrom and being of a size and shape to allow a user to grasp the gripping member 28 to move, adjust, operate, control, or otherwise manipulate the body portion 20. The gripping member 28 may extend from a side of the body portion 20 and may also be coupled to the body portion 20 at a top or bottom thereof, depending on whether the device will be utilized for a top row of teeth or a bottom row of teeth, which will be described in greater detail.

Grasping the gripping member 28 may allow a user to insert and/or remove the body portion 20, and therefore the oral hygiene device 10, from the user's oral cavity. Exerting force on the gripping member 28 may allow a user to maneuver and manipulate the oral hygiene device 10, to be described in further detail herein, within the user's oral cavity. The gripping member 28 may further comprise an opening 29 therein that allows a user's fingers to contact one another even as the user's fingers grasp the gripping member 28. By allowing the user's fingers to contact one another while at the same time gripping the gripping member 28, the user may achieve a firmer, non-slip grasp on the gripping member 28 to thereby exert greater force and control on the oral hygiene device 10.

Embodiments of the oral hygiene device 10 may further comprise opposing sidewalls, or first and second sidewalls 24 and 26, extending from the base 22 of the body portion 20. The first sidewall 24 may extend from an edge portion of the first surface 25 of the base 22 and the second sidewall 26 may extend from an edge portion on an opposite edge of the first surface 25 of the base 22, such that the second sidewall 26 opposes the first sidewall 24. The first and second sidewalls 24 and 26 may extend from the base 22 for a predetermined distance and may also run along a predetermined length of the base 22, including up to the entire length of the base 22 from the distal end 21 to the opposing distal end 23. Described another way, the first and second sidewalls 24 and 26 may each rise up off of opposite edge portions of the first surface 25 of the base 22 and run along a substantial length of the base 22, such that the first and second sidewalls 24 and 26 define an opening, chasm, cavity, or gap 30 therebetween along at least a portion of the length of the base 22. The gap 30 may have a depth defined by the height of the first and second sidewalls 24 and 26 off of the first surface 25 of the base 22. The gap 30 may also have a width defined by the distance between the opposing first and second sidewalls 24 and 26. The width may be substantially constant, or in the alternative may vary, along the length of the base 22 or along the length of the sidewalls 24 and 26. The first and second sidewalls 24 and 26 may further comprise holes or openings therein at a position proximate the distal ends 21 and 23 or proximate the securing mechanism 43. The holes or openings may be configured to receive therethrough the material 50 for assisting in securing or anchoring the material 50 to the device 10.

Embodiments of the oral hygiene device 10 may further comprise notches 40 positioned in one or both of the first and second sidewalls 24 and 26. The notches 40 may be located at or near the top edge of each of the sidewalls 24 and 26. The notches 40 may be slight or small indentations, cracks, crevices, clefts, notches, or depressions in the top edge portions of the first and second sidewalls 24 and 26. The notches 40 may have a depth, size, and shape that allow a threadable, thread-type, or fibrous material 50 to be inserted therein and retained thereby, as illustratively depicted in FIG. 5, such that the thread-type or fibrous material 50 does not substantially slide within the notch 40 or notches 40. In certain embodiments, the notches 40 may be shaped in a v-type pattern with the point of the v-shape facing toward the base 22, so that as the material 50 engages the notch 40 the material 50 may be engaged by and rest securely and firmly in the lower point of the v-shape. Moreover, the side edges of the notches 40 may also be abrupt or non-rounded edges to further engage the material 50 and hold the material 50 firmly in place once set.

Figure 5:
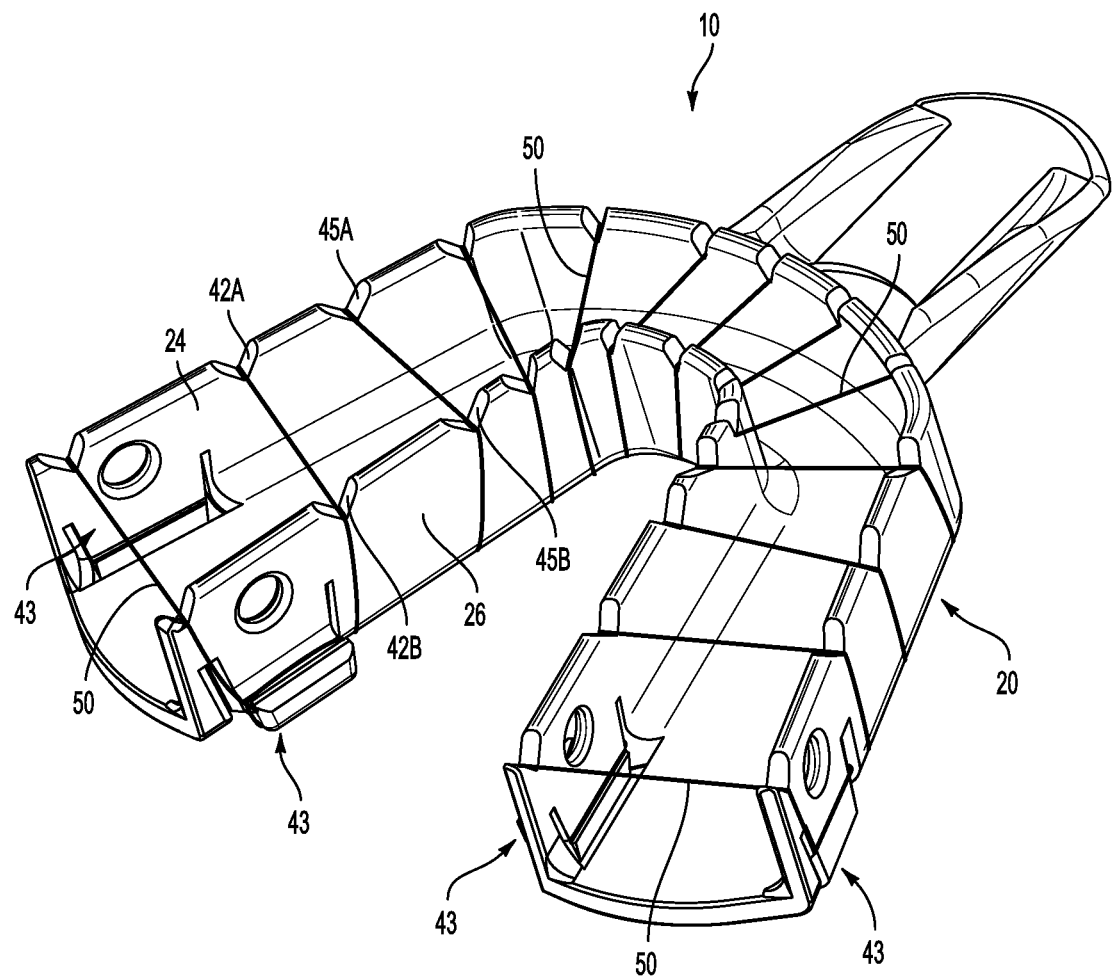
FIG. 5 is a perspective view of an embodiment of the oral hygiene device and a material coupled thereto in accordance with the present disclosure.

Embodiments of the oral hygiene device 10 may further comprise the notches 40 being arranged in corresponding pairs of notches, one on each sidewall 24 and 26. For example, as depicted in FIG. 5, a first notch 42A of a first notch pair may be positioned in the first sidewall 24 and a second notch 42B of the first notch pair may be positioned in the second sidewall 26. Further in example, advancing down the length of the sidewalls 24 and 26 away from the first notch pair, a first notch 45A of a second notch pair may be positioned in the first sidewall 24 and a second notch 45B of the second notch pair may be positioned in the second sidewall 26. Advancing further along the sidewalls 24 and 26, there may be positioned additional notch pairs having a first notch in the first sidewall 24 and a second notch in the second sidewall 26. Having a plurality of notch pairs positioned at various points along the lengths of the first and second sidewalls 24 and 26 allows the material 50 to be threaded, engaged, or placed between corresponding notch pairs, such as between notch pair 42A and 42B as well as between 45A and 45B, to span the gap 30 between these notch pairs at various points and positions along the length of the base 22, and thus the device 10. Each of the notch pairs may also be color-coordinated to match one another. For example, the first notch 42A and the second notch 42B of the first notch pair may be color-coded in a first color, such as, for example, red. Likewise, the first notch 45A and the second notch 45B of the second notch pair may be color-coded in a second color, such as, for example, blue. In like manner, additional notch pairs along the sidewalls 24 and 26 may also be color-coded with additional colors to thereby visibly coordinate with one another to visibly indicate to the user which notches correspond to one another as a notch pair. Any number of colors may be used to highlight corresponding notches of the notch pairs, so long as the corresponding notches are the same color to indicate the correspondence. Also, for convenience and simplicity, two colors may alternate along the length of the sidewalls 24 and 26 between neighboring notch pairs to separate and highlight corresponding notch pairs of the device 10.

Embodiments of the oral hygiene device 10 may further comprise a securing mechanism 43 for anchoring, securing, holding, or otherwise retaining the material 50 on the device 10. The securing mechanism 43 may be positioned at or near the base 22 of the body portion 20 or at or near the opposing sidewalls 24 and 26. Embodiments of the oral hygiene device 10 may further comprise a plurality of securing mechanisms 43 positioned at or near the base 22 of the body portion 20 at or near the distal ends 21 and 23 at or near the location where the opposing sidewalls 24 and 26 contact the base 22.

The securing mechanism 43 may include one or more of an aperture 44, a catch tab 46, and a catch 48. The aperture 44 may be an opening, gap, hole, space, orifice, or cavity configured in the device 10 near the location where the opposing sidewalls 24 and 26 contact the base 22. The aperture 44 may be of a size and shape to permit the material 50 to pass therethrough, as needed, to facilitate threading or loading of the fibrous material 50 onto the device 10 and in the notches 40. The aperture 44 may also be sized and shaped to permit the catch tab 46 to be positioned within the aperture 44. The catch tab 46 may be a part of the body portion 20 that resides in the aperture 44 and extends at least partially outward from the body portion 20. The catch tab 46 may be a part of the base 22 or a part of the respective sidewall 24 or 26, or parts of both. As depicted in the Figures, the catch tab 46 may be a portion of the sidewall 24 or 26 that extends into the aperture 44 and also extends at least partially away from the body portion 20, thus creating a lip 47.

The lip 47 may be configured to receive thereon the material 50 so as to anchor or otherwise secure the material 50 to the device 10. The lip 47 may be further configured with a raised outer edge 49 to help prevent the material 50 from sliding off or otherwise disengaging from the lip 47 and the catch tab 46. For example, a free end of the material 50 may be wound about the lip 47 several times until the material 50 binds on itself against the lip 47 due to friction fit. Using the lip 47 and catch tab 46 as anchors, the material 50 may then be wound about the device 10, which is to be explained in greater detail herein. The configuration of the aperture 44 and the catch tab 46 may define therebetween a catch 48.

The catch 48 may be a slit, groove, slot, gash, or opening wherein the material 50 may also be inserted to further anchor or secure the material 50 to the device 10. The catch 48 may be open to the aperture 44 and reduce in width as the catch 48 moves away from the aperture 44. Indeed, the catch 48 may be defined by the catch tab 46 and the respective sidewall 24 or 26 from which the catch tab 46 extends, wherein the catch 48 is defined on either side of the catch tab 46 between the catch tab 46 and the sidewall 24 or 26. The catch 48 may have a length running from the aperture 44 to the point where the catch tab 46 meets the respective sidewall 24 or 26 and may have a width wherein the material 50 may be inserted. The width of the catch 48 may be reduced to zero at the point where the catch tab 46 meets either of the sidewalls 24 or 26. As such, the material 50 may be inserted within the catch 48 and the narrowing width may assist in further securing the material 50 to the catch 48, and thus the device 20, by friction fit.

Figure 6:
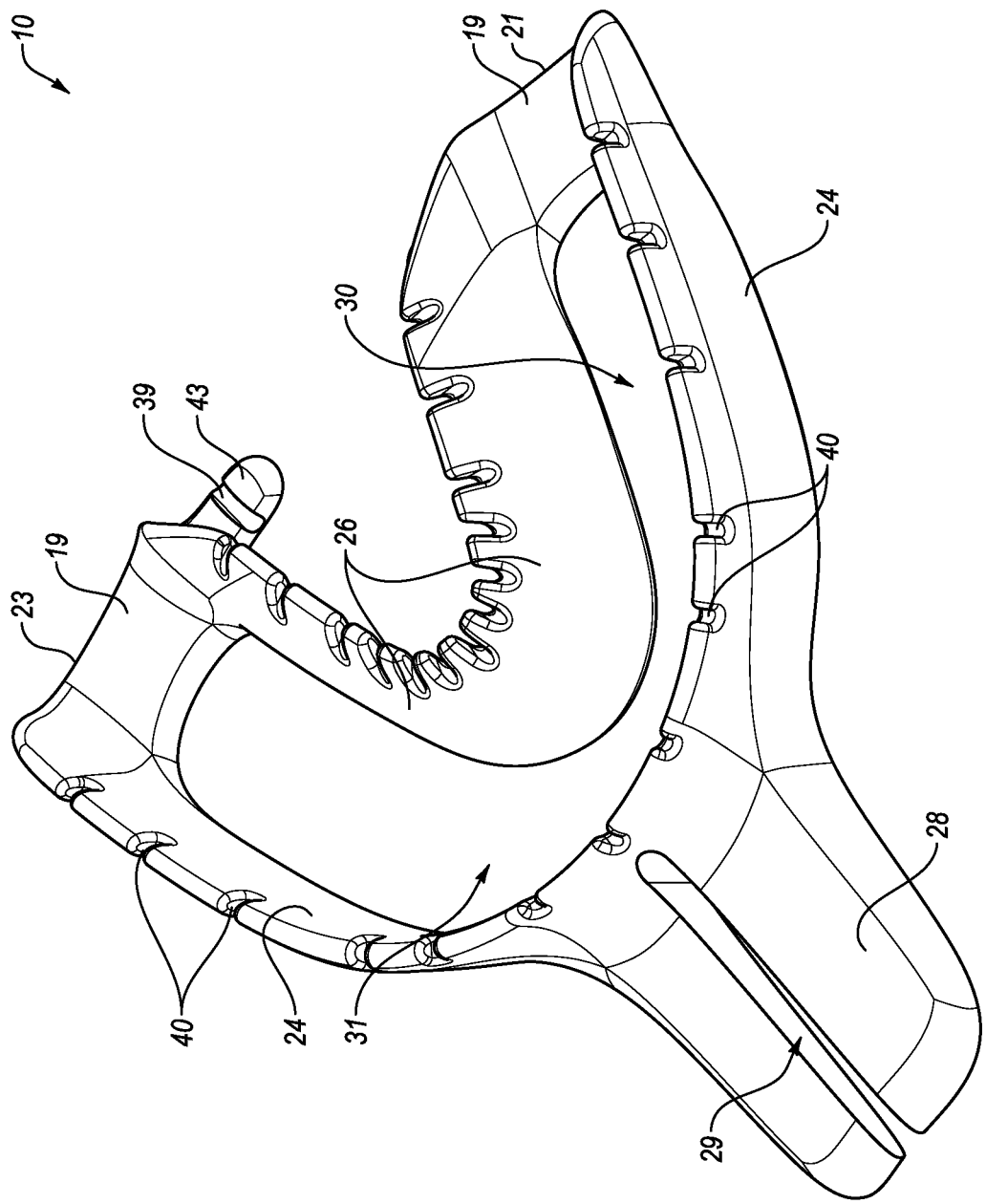
FIG. 6 is a perspective view of an embodiment of an oral hygiene device in accordance with the present disclosure.
Figure 7:
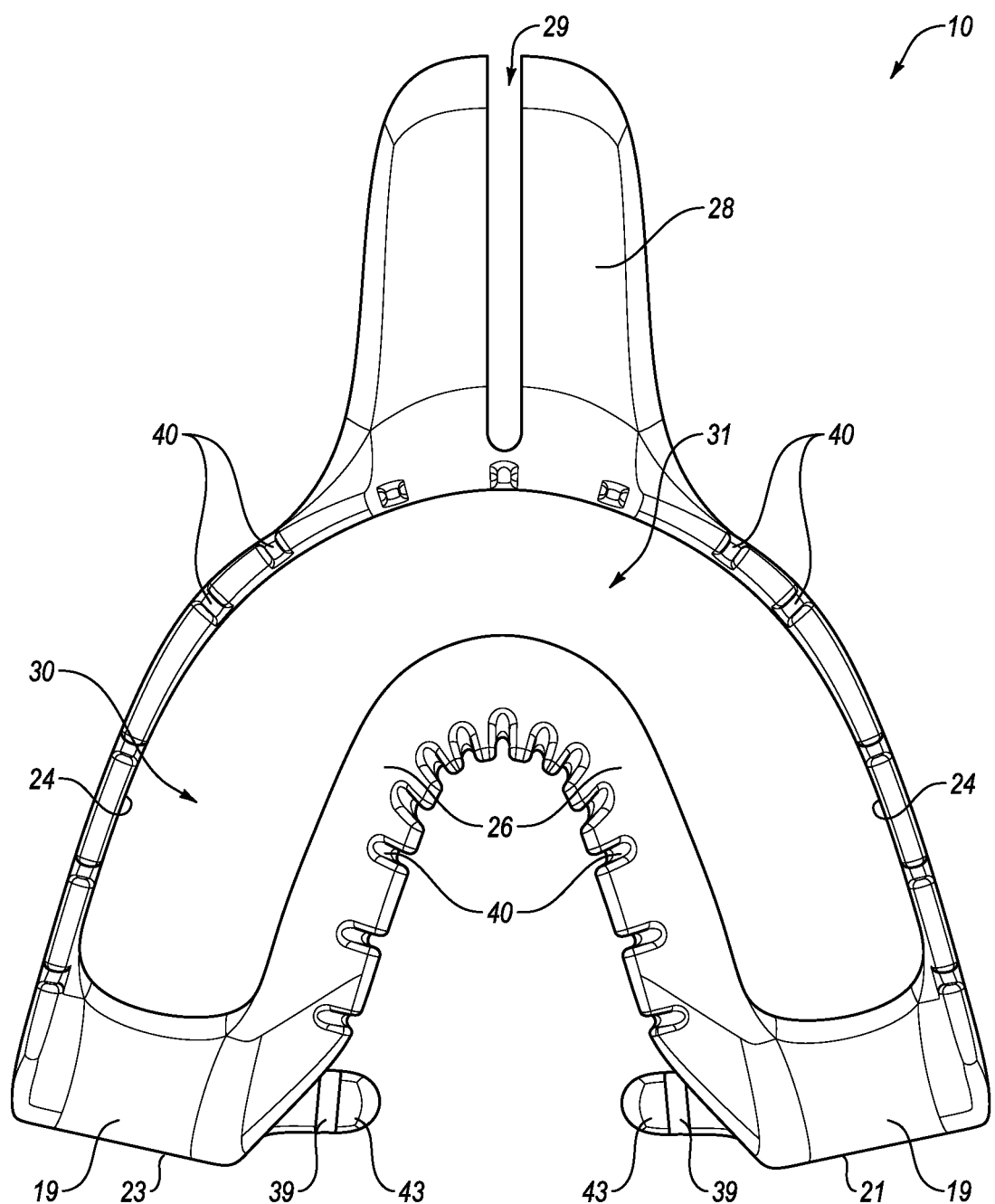
FIG. 7 is a top view of an embodiment of the oral hygiene device in accordance with the present disclosure.
Figure 8:
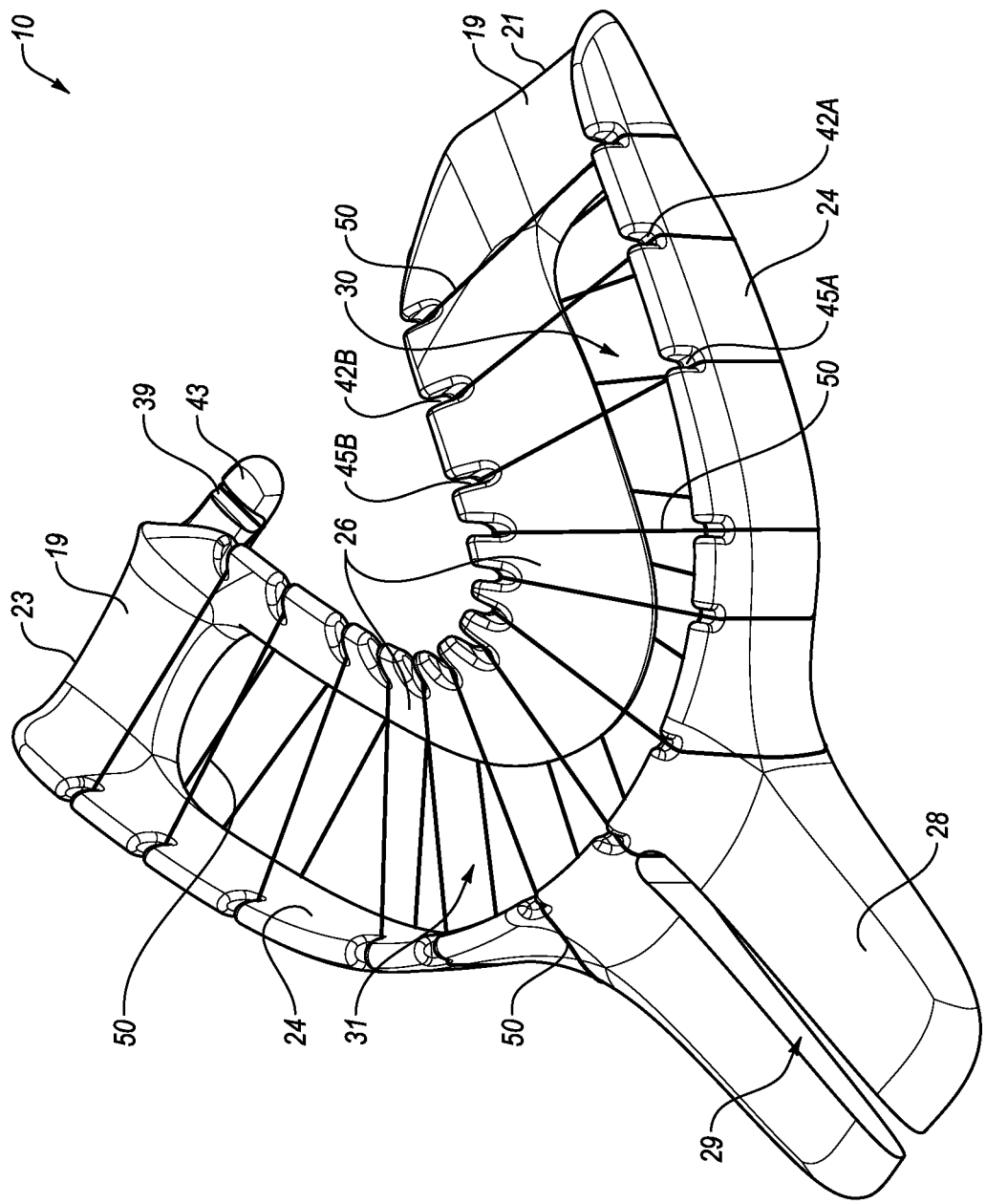
FIG. 8 is a perspective view of an embodiment of the oral hygiene device and a material coupled thereto in accordance with the present disclosure.

Referring to the drawings, FIGS. 6-8 depict an illustrative embodiment of an oral hygiene device 10 having many features of previous embodiments and a few other features. For example, embodiments of the oral hygiene device 10 may comprise, among other features, astability member 19, opposing sidewalls 24 and 26, and notches 40.

Embodiments of the oral hygiene device 10 may comprise opposing sidewalls, or first and second sidewalls 24 and 26 that are set at distance from one another with an aperture 31 therebetween. The first and second sidewalls 24 and 26 may each have a length running from the distal end 21 to the opposing distal end 23 of the device 10. The first and second sidewalls 24 and 26 may be formed in a substantially u-shaped configuration, similar to the pattern and/or shape of the dental anatomy of a human being. Embodiments of the device 10 may comprise the first and second sidewalls 24 and 26 being positioned at a distance from one another in this u-shape configuration to thereby establish and/or define the gap 30 therebetween, the gap 30 running along at least a portion, or in some embodiments the entire length, of the first and second sidewalls 24 and 26 from the distal end 21 to the opposing distal end 23. The gap 30 may have a depth defined by the height of the first and second sidewalls 24 and 26. Embodiments of the device 10 may further comprise the first and second sidewalls 24 and 26 being angled with respect to one another. For example, the second sidewall 26 may be slanted with respect to the first sidewall 24. If the first sidewall 24 is substantially vertical or plumb, then the second sidewall 26 may be angled or slanted therefrom. As depicted in FIG. 6, the second sidewall 26 may be slanted slightly toward the interior of the device from the bottom of the device 10 near the aperture 31 to the top of the device 10 near the notches 40. In this way, the sidewalls 24 and 26 may be customizable to the user's dental and mouth anatomy.

Embodiments of the device 10 may further comprise the aperture 31 being defined between the first and second sidewalls 24 and 26, such that the gap 30 is open on not only the top side but the bottom side. In other words, the aperture 31 may be configured of a size and shape to create an opening in the base or underside of the device 10 between the first and second opposing sidewalls 24 and 26. With the gap 30 being open to both the top side and the bottom side, access to the device 10 may be enhanced, and particularly with regard to cleaning the device. Indeed, the interior sides of the first and second sidewalls 24 and 26 may be easily accessed through either the top side of the gap 30 or the bottom side of the gap 30.

Embodiments of the oral hygiene device 10 may comprise a stability member 19. The stability member 19 may have a flat, level, even, uniform, or substantially smooth surface. Alternatively, the stability member 19 may have a textured surface or non-uniform surface features. The stability member 19 may be positioned between the first and second sidewalls 24 and 26 at or proximate one or more of the distal ends 21 and 23. The stability member 19 may additionally be placed at a lower end or edge of the first and second sidewalls 24 and 26 between the first and second sidewalls 24 and 26. In this way, the stability member 19 may provide some structural rigidity or support to the sidewalls 24 and 26 at the distal ends 21 and 23. The size and shape of the stability member 19 may determine the limits of the structural rigidity of the device 10. For example, the longer the stability members 19 along the length of the sidewalls 24 and 26, the stronger the device 10. Further in example, the size and shape of the stability member 19 may additionally define the size and shape of the aperture 31. The aperture 31 may be positioned along the lower ends of the first and second sidewalls 24 and 26 between the stability member 19 near the distal end 21 and the stability member 19 near the opposing distal end 23. Thus, the larger the stability member 19, the smaller the aperture 31, and vice versa.

Embodiments of the oral hygiene device 10 may further comprise a gripping member 28 extending from at least one of the sidewalls 24 and 26 of the device 10. As depicted, the gripping member 28 may extend outward from a side of the first sidewall 24. The gripping member 28 may be coupled to the first sidewall 24 at a top or bottom edge thereof, depending on whether the device will be utilized for a top row of teeth or a bottom row of teeth, which will be described in greater detail. The gripping member 28 may be configured of a size and shape to allow a user to grasp the gripping member 28 to move, adjust, operate, control, or otherwise manipulate the device 10.

Grasping the gripping member 28 may allow a user to insert and/or remove the oral hygiene device 10 from the user's oral cavity. Exerting force on the gripping member 28 may allow a user to maneuver and manipulate the oral hygiene device 10, to be described in further detail herein, within the user's oral cavity. The gripping member 28 may further comprise an opening 29. The opening 29 may be a slit, slot, or opening that runs substantially along the length of the gripping member 28. The opening 29 may also open to the edge of the gripping member 28, such that the opening 29 can be accessed from the exterior of the gripping member 28. Further, the opening 29 may be configured to receive therein the material that can be added to the device 10. The opening 29 may be configured to have the material 50 inserted therein and substantially hold or maintain the material 50 in place. The opening 29 may permit a user to thread only a partial portion of the device 10 with the material 50, say, for example, from the distal end 21 to the gripping member 28.

Embodiments of the oral hygiene device 10 may further comprise notches 40 positioned in one or both of the first and second sidewalls 24 and 26, similarly to the notches 40 previously described with regard to additional embodiments of the device 10. For example, the notches 40 may be located at or near the top edge of each of the sidewalls 24 and 26 and opposite to the aperture 31 near the bottom edge of the sidewalls 24 and 26. The notches 40 may be slight or small indentations, cracks, crevices, clefts, notches, or depressions in the top edge portions of the first and second sidewalls 24 and 26. The notches 40 may have a depth, size, and shape that allow a threadable, thread-type, or fibrous material 50 to be inserted therein and retained thereby, as illustratively depicted in FIG. 8, such that the thread-type or fibrous material 50 does not substantially slide within the notch 40 or notches 40. In certain embodiments, the notches 40 may be shaped in a v-type pattern with the point of the v-shape facing toward the base 22, so that as the material 50 engages the notch 40 the material 50 may be engaged by and rest securely and firmly in the lower point of the v-shape. Moreover, the side edges of the notches 40 may also be abrupt or non-rounded edges to further engage the material 50 and hold the material 50 firmly in place once set. The notches 40 may include nooks, crannies, hooks, or the like, that may assist in holding the material 50 to the device 10. For example, the nook, hook, or the like may be configured to prevent the material 50 from vertically lifting off of the device, or out of the notch 40, when force is applied by the user during use.

Further in example, embodiments of the oral hygiene device 10 may further comprise the notches 40 being arranged in corresponding pairs of notches, one on each sidewall 24 and 26. For example, as depicted in FIG. 8, a first notch 42A of a first notch pair may be positioned in the first sidewall 24 and a second notch 42B of the first notch pair may be positioned in the second sidewall 26. Further in example, advancing down the length of the sidewalls 24 and 26 away from the first notch pair, a first notch 45A of a second notch pair may be positioned in the first sidewall 24 and a second notch 45B of the second notch pair may be positioned in the second sidewall 26. Advancing further along the sidewalls 24 and 26, there may be positioned additional notch pairs having a first notch in the first sidewall 24 and a second notch in the second sidewall 26. Having a plurality of notch pairs positioned at various points along the lengths of the first and second sidewalls 24 and 26 allows the material 50 to be threaded, engaged, or placed between corresponding notch pairs, such as between notch pair 42A and 42B as well as between 45A and 45B, to span the gap 30 between these notch pairs at various points and positions along the length of the base 22, and thus the device 10. Each of the notch pairs may also be color-coordinated to match one another. For example, the first notch 42A and the second notch 42B of the first notch pair may be color-coded in a first color, such as, for example, red. Likewise, the first notch 45A and the second notch 45B of the second notch pair may be color-coded in a second color, such as, for example, blue. In like manner, additional notch pairs along the sidewalls 24 and 26 may also be color-coded with additional colors to thereby visibly coordinate with one another to visibly indicate to the user which notches correspond to one another as a notch pair. Any number of colors may be used to highlight corresponding notches of the notch pairs, so long as the corresponding notches are the same color to indicate the correspondence. Also, for convenience and simplicity, two colors may alternate along the length of the sidewalls 24 and 26 between neighboring notch pairs to separate and highlight corresponding notch pairs of the device 10.

Embodiments of the oral hygiene device 10 may further comprise a securing mechanism 43 for anchoring, securing, holding, or otherwise retaining the material 50 on the device 10. As depicted in FIGS. 6-8, the securing mechanism 43 may be positioned at or near the distal ends 21 and 23 of the opposing sidewalls 24 and 26. Embodiments of the oral hygiene device 10 may further comprise a plurality of securing mechanisms 43 positioned at or near the distal ends 21 and 23 of the opposing sidewalls 24 and 26. The securing mechanism 43 may extend inwardly from an interior surface of the second sidewall 26 toward the opposing interior surface of the second sidewall 26 on an opposite side of the device 10. In other words, the securing mechanism may extend inwardly from the device toward the tongue of the user or the interior of the oral cavity. Embodiments of the securing mechanism 43 may comprise a channel 39 positioned in the securing mechanism 43 and configured to receive therein the material 50. In other words, a user may wrap the material 50 about the securing mechanism 43 within the channel 39 and the channel 39 will serve to secure the material thereto by friction fit.

Moreover, embodiments of the oral hygiene device 10 may further comprise a sleeve, tab, flap, snap, clip, or fastener (not depicted) that is configured to cooperate with the channel 39 and/or securing mechanism 43 to releasably secure the material 50 thereto. For example, a user may place a portion of the material 50 within the channel 39 and operate the fastener (not depicted), such as a sleeve that slides onto the securing mechanism 43 or a flap, snap, clip, or the like, that folds over the channel 39, to secure the material 50 to the channel 39 and/or the securing mechanism 43. The fastener (not depicted) may be formed integrally with the device 10 or may be an additional member that is configured to operate with the device 10, as described herein.

Embodiments of the oral hygiene device 10 may be customizable to a user. For example, each user of the device 10 will have a unique gum line, tooth structure and tooth placement, not to mention unique spacing between teeth and neighboring teeth. Therefore it is desirable to permit the device 10 to be adaptable and customizable to each user's unique size, shape, and dental configuration. As a result, embodiments of the device 10 contemplate that each feature of the device 10 such as, for example, the body portion 20, the base 22, the opposing sidewalls 24 and 26, the gap 30, the aperture 31, the stability member 19, and the notches 40 may each be sized, shaped, configured, and positioned respectively on the device 10 to correspond to the unique size and shape of a user's mouth, teeth, and gums. Other elements such as, for example, the gripping member 28 and the securing mechanisms 43 may also be customized and positioned on the device 10 where needed, according to circumstance and the individual customization.

Embodiments of the dental hygiene device 10 and its associated methods may comprise taking an impression of the user's dental structure to identify the dental structure or dental model of a user. Impressions can be made for the top row of teeth, the bottom row of teeth, or both rows of teeth—top and bottom. The impressions may be obtained using conventional methods or digitally. Once obtained, the impressions may be used to design a model of the user's dental structure. The model may be a digital model, such as a 3-D CAD rendered model, or a physical model, such as a plaster casting. A digital model may be obtained by using computer software to take a 3-D digital scan of the negative impressions of the dental model, which can then be turned around and used to build the software-enabled digital 3-D model of the user's actual teeth or dental structure. On the other hand, the physical model may be obtained by filling the negative impressions of the dental model with plaster, which, once dried, will be in the form of the unique dental structure of the particular user. Using either model, measurements can be taken of the user's mouth, teeth, and overall dental structure, including for example the size, depth, curvature, shape, angles, and spaces of and between each tooth. Of course, using the digital model, the measurements can be obtained digitally through software, and using the physical model, the measurements can be obtained by physical measurement performed by trained technicians.

Based on these specific and custom measurements, the device 10 may be designed and constructed for each particular user. Further thereto, because each user may have a different dental structure for the top row of teeth and the bottom row of teeth, a uniquely designed and customized device 10 may be configured for each of the user's top row of teeth and bottom row of teeth. For example, a custom device 10, for either top or bottom rows of teeth, may require that the sidewalls 24 and 26 be of different sizes or heights, the gap 30 be a varying width or depth, the base 22 and body portion 20 be a larger or smaller size, and/or the notches 40 having a unique shape or being placed at custom locations along each of the sidewalls 24 and 26. There are any number of customizations that may be applied to each device 10 during design and manufacture for each particular user, at least substantially, if not entirely, based on the custom measurements obtained from the 3-D or plaster models of the user's dental structure.

The device 10 may be constructed, crafted, produced, and/or manufactured using one or more of the methodologies and techniques described herein below. The device 10 may also be printed using 3-D printing technologies. The device 10 may be comprised of materials from one or more of the materials described herein below. The device 10 may also be comprised of PLA (polylactide or polyactic acid filament), a biodegradable medical grade dental thermoplastic BPA-free and Latex-free material derived from renewable sources (or medical grade copolymer BPA-free Latex-free or FDA-compliant thermoplastic elastomer BPA-free Latex-free), ABS Plastic (FDA approved, medical grade filament or non-medical grade filament), resin (liquid: high detail, paintable, transparent), and/or nylon (polyamide). These materials are FDA compliant, safe and non-invasive substances that comply with medical and dental safety specifications, and are the same materials for dental products used in the mouth such as mouth guards, anti-snore guards and bite guards.

As previously mentioned, embodiments of the oral hygiene device 10 may comprise the notches 40 being positioned in an upper portion or top portion of each sidewall 24 and 26 and may be placed at various locations along their respective lengths. Additionally, the notches 40 may be arranged in notch pairs, wherein a first notch 42A of the notch pair is positioned in the first sidewall 24 and the second notch 42B of the notch pair is positioned in the second sidewall 26. The first and second notches 42A and 42B of each notch pair may be positioned at strategic locations on the respective sidewalls 24 and 26, and may be designed to receive therein the material 50 in a threaded arrangement. In other words, when the material 50 is to be threaded onto the device 10, the material 50 may be threaded through, into, or over each notch pair in succession (i.e., between notch pair 42A and 42B as well as notch pair 45A and 45B), such that the material 50 bridges the gap 30 by each notch pair at a desired and predetermined location and at a desired and predetermined angle for each notch pair, based on and calculated from the measured dimensions obtained from the user's model dental structure, described above.

For example, a user may have large gaps or spaces between individual teeth or a user may have crooked teeth next to one another. In every such instance, the design and manufacture of the device 10 may account for these unique circumstances and it may thereby be determined to position the notches 40 and notch pairs at calculated positions on each sidewall 24 and 26 to give the material 50 that bridges the gap 30 therebetween the best chance or opportunity to be inserted between the individual teeth of the user when the device 10 is placed into the user's mouth and force is exerted thereon to insert the material 50 between the user's teeth according to its intended purpose. To describe the orientation of the notch pairs in another way, the angle of the material 50 running over the gap 30 with respect to the sidewalls 24 and 26 may be different between one or more notch pairs, or even every notch pair; the material 50 that bridges the gap 30 at one particular notch pair may be perpendicular to the sidewalls 24 and 26 but, in comparison, may be at an acute angle to the sidewalls 24 and 26 between another particular notch pair. As such, the orientation of one or more, or all, of the notch pairs or notches 40 may be angled (i.e., not perpendicular) with respect to the orientation of the sidewall. Indeed, the configuration of the notches 40 and the notch pairs on the device 10 may be as diverse as the users themselves.

With regard to the placement of the material 50 on the device, embodiments of the oral hygiene device 10 and its associated methods may comprise the material 50 being releasably coupled to the device 10 to span the gap 30 at a plurality of locations defined by the notches 40, and in particular to the notch pairs, so that as the user places the threaded device 10 in his/her mouth the material 50 may be concurrently applied between each of the user's teeth. The device 10 therefore allows a user to utilize a single device 10 to clean between each of the user's teeth at the same time. For example, a user may utilize a custom device 10 for the top row of teeth, and may also user another custom device 10 for the bottom row of teeth. In this way, the difficulty and tedious nature of flossing is effectively eliminated and users are much more likely to floss their teeth.

With reference to FIGS. 5 and 8, embodiments of the oral hygiene device 10 may comprise the material 50 being threaded through at least one of, if not all, the notch pairs on the device 10. The material 50 may be threaded by wrapping the material 50 about the circumference of the body portion 20 of the device 10. As illustratively depicted, in FIGS. 5 and 8, the material 50 may first be coupled by friction force to one or more of the securing mechanisms 43, catch tabs 46 and/or catches 48 on one distal end (i.e., 21) of the device 10 and thereafter wrapped around the device 10 in successive circles, making sure to thread the material 50 through each successive notch pair each time the material 50 is wrapped about the device 10. Once the material 50 has been wrapped around the device 10 enough times to thread the material over the gap 30 between each notch pair, the material 50 may be coupled to one or more of the catch tabs 46 and/or catches 48 on the opposite distal end (i.e., 23) of the body 22 from where the material 50 was initially coupled. Also, the material 50 may be threaded through one or more of the holes or openings in the sidewalls 24 and 26 proximate the securing mechanism 43 to assist in securing or anchoring the material 50 to the device 10, in conjunction with the features of the securing mechanism 43. Alternatively, the material 50 may be threaded about the device 10 multiple times through each notch pair to potentially strengthen the rigidity of the material 50 over the gap 30. Alternatively, the material 50 may be threaded about the device 10 in a custom manner, wherein the user determines which specific notch pairs of the total notch pairs the user will thread the material 50 through and which notch pairs the user might skip.

Figure 9:
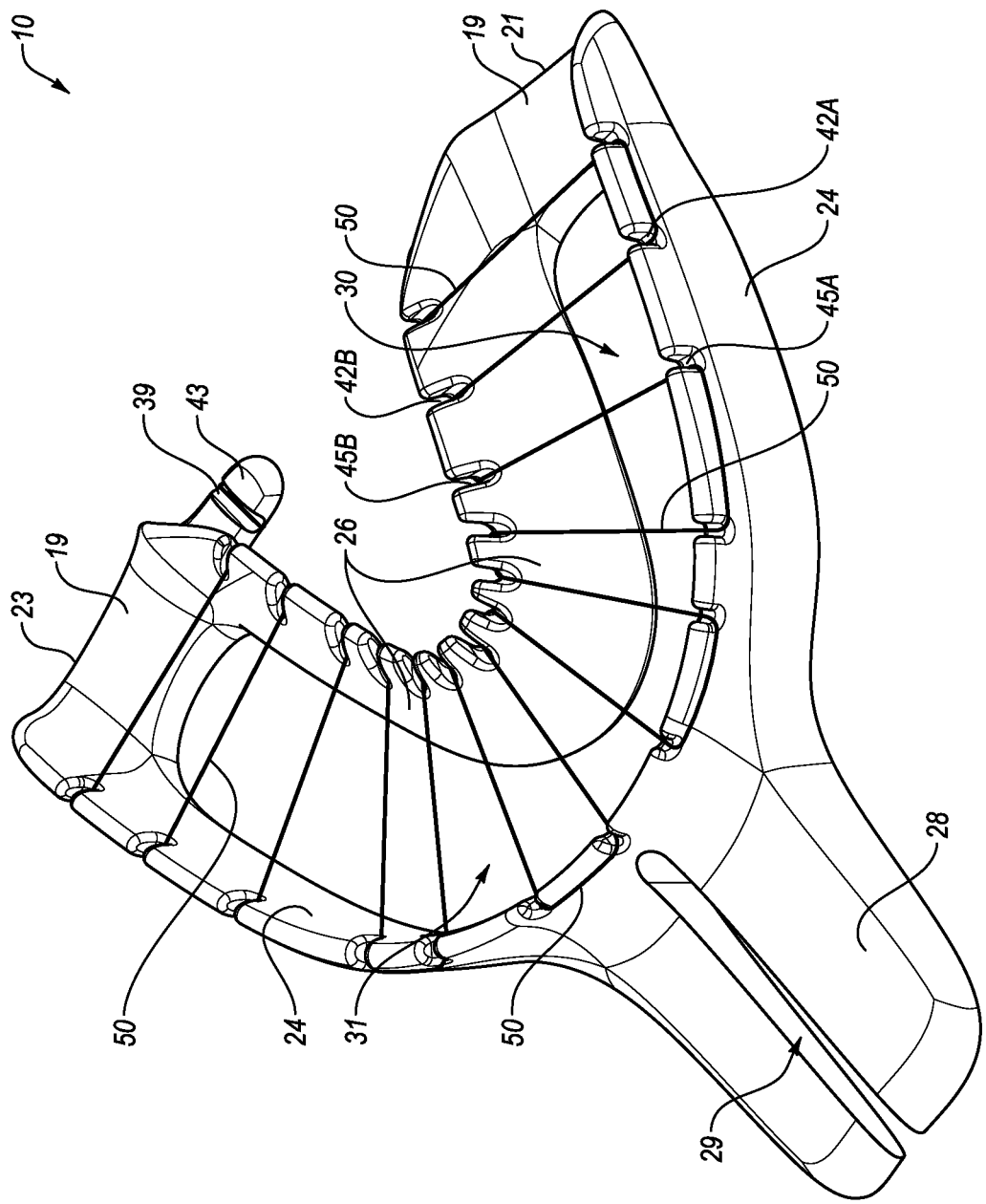
FIG. 9 is a perspective view of an embodiment of the oral hygiene device and a material coupled thereto in accordance with the present disclosure.

Alternatively, instead of the material 50 being wrapped about the device 10, the material 50 may be threaded on the device 10 along the top of the sidewalls 24 and 26 and between corresponding notch pairs in a sort of a zig-zag pattern. For example, as depicted in FIG. 9, a first notch 42A of a first notch pair may be positioned in the first sidewall 24 and a second notch 42B of the first notch pair may be positioned in the second sidewall 26. Further in example, advancing down the length of the sidewalls 24 and 26 away from the first notch pair, a first notch 45A of a second notch pair may be positioned in the first sidewall 24 and a second notch 45B of the second notch pair may be positioned in the second sidewall 26. Advancing further along the sidewalls 24 and 26, there may be positioned additional notch pairs having a first notch in the first sidewall 24 and a second notch in the second sidewall 26. Having a plurality of notch pairs positioned at various points along the lengths of the first and second sidewalls 24 and 26 allows the material 50 to be threaded, engaged, or placed between corresponding notch pairs, such as between notch pair 42A and 42B as well as between 45A and 45B, to span the gap 30 between these notch pairs at various points and positions along the length of the base 22, and thus the device 10.

Also, because the material 50 is releasably coupled to the device 10, the user may remove and apply the material 50 to the device 10 as needed, as determined by the user according to preference, or as directed by a dentist.

Embodiments of the oral hygiene device 10 may further comprise the material 50 being permanently affixed to the device 10. Thus, instead of the notches 40 being strategically positioned in the sidewalls 24 and 26 to form the corresponding notch pairs, the material 50 may be embedded in the sidewalls 24 and 26. By the material 50 being embedded, or otherwise affixed, to the sidewalls 24 and 26, there is no need for the notches 40. Nevertheless, the placement of the material 50 on the device 10 in a fixed manner is dependent still upon the specific and custom design configuration of each user in the means and manner described herein. In other words, the material 50 may be affixed to the sidewalls 24 and 26 of the device 10 in the positions where the notches 40 would have been if the material 50 where removable. The material 50 may be affixed to the device 10 during manufacture of the device. Alternatively, the material 50 may be affixed to the device 10 by adhesive, such as medical grade epoxy, after manufacture of the device 10. As such, the device 10 may yet be manufactured with small notches 40 in the sidewalls 24 and 26 to indicate where the permanent material 50 should be affixed to construct the corresponding notch pairs. The material 50 that is to be permanent may be comprised of carbon fiber strands, specially-manufactured dental floss, nylon strands, and/or wire strands. The thickness and rigidity of the material 50 that is to be permanent can be adjusted during construction of the device 10 for each user based on the user's dental structure. For example, the material 50 that is to be permanent on the device 10 may vary according to gaps in the user's teeth or angles of the user's teeth. The material 50 between one notch pair may be a wire having a thickness, whereas the material between another notch pair may be carbon fiber strands with a thickness greater than the thickness of the wire. In other words, the types, properties, and thickness of the material 50 used between each corresponding notch pair may vary according to the custom design of the device 10 for each user based on the user's specific dental structure. Embodiments of the device 10 having a permanent material 50 attached thereto may be designed for prolonged and repetitive use.

Embodiments of the oral hygiene device 10 and its associated methods may comprise threading the manufactured device 10 with the material 50 and testing the threaded device 10 on the model of the user's teeth for proper fit and alignment, prior to sending the custom device 10 to the user. For example, where the device 10 has been designed and manufactured according to digital scans and digital measurements, the digital replication of the user's teeth may be used to create and/or produce a physical replica of the user's teeth. Indeed, the replica may be manufactured according to the methods described herein below, and may be manufactured by 3-D printing methods and systems. Thereafter, the device maker may use the physical replica to test the accuracy and effectiveness of the custom device 10, prior to sending the custom device 10 to the actual user. Further in example, where the device 10 has been designed and manufactured from the measurements acquired from the plaster casting of the user's teeth measurements, the device maker may use the plaster physical replica to test the accuracy and effectiveness of the custom device 10, prior to sending the custom device 10 to the actual user.

Once the user has received the device 10 and the device 10 is threaded by the user with the material 50, the user may insert the device 10 into the user's mouth and apply force to the device 10 to permit the material 50 to be inserted between each of the spaces between the user's teeth. The force may be applied by hand, may alternatively be applied by the operation of the user's jaw, or may be a combination of both. Once the material 50 is inserted between the user's teeth, the device 10 may also be moved up and down such that the material 50 may move up and down the sides of the user's teeth. This method of use can be repeated as needed or as directed by a dentist. Moreover, once the material 50 has reached its usable limit, the old and used material 50 may be removed from the device 10 and new material 50 can be inserted thereon. This process may be repeated over and over again for continued use.

Embodiments of the oral hygiene device 10 may comprise the user ordering a kit via the internet or other media, wherein the kit may be sent to the user's home by mail or other postal carrier and the user can use the kit to make a dental impression of the user's teeth, both top and bottom rows. Instructions may be included to instruct the user on how to take the impressions, or a website link may be included to direct the user to a website containing instructions or an instructional video. The impressions may thereafter be sent by pre-paid envelope to the maker of the device 10, so that the maker of the device 10 can first create the model of the user's dental structure, take measurements of the dental structure, and thereafter produce a custom designed device 10 for the particular user. The custom designed devices 10 may then be sent or delivered to the user for use and application. As an alternative to using the kit by mail, a user may also have impressions of his/her teeth performed and made at a dentist's office. Thereafter, the dentist may perform the 3-D scans of the impressions and send the scans (i.e., digital files) to the device maker by secure transmission (i.e., secure email, server, Dropbox, Sharefile or other secure cloud-based file sharing medium). The dentist may alternatively send the impressions to the device maker by mail in a pre-paid envelope. The device maker may then design and manufacture the custom devices 10, one for each of the top and bottom rows of teeth, based on the scans or impressions. Again, the custom designed devices 10 may then be sent or delivered to the user for use and application.

While this disclosure has been described in conjunction with the specific embodiments outlined above, it is evident that many alternatives, modifications and variations will be apparent to those skilled in the art. Accordingly, the preferred embodiments of the present disclosure as set forth above are intended to be illustrative, not limiting. Various changes may be made without departing from the spirit and scope of the present disclosure, as required by the following claims. The claims provide the scope of the coverage of the present disclosure and should not be limited to the specific examples provided herein.

What is claimed is:

1. An oral hygiene device comprising:
    first and second opposing sides, the first and second opposing sides defining a distance therebetween; and
    a plurality of corresponding notch pairs, wherein each corresponding notch pair has a first notch positioned in the first opposing side and a second notch positioned in the second opposing side, wherein the first opposing side is configured to be disposed near a user's inner check during use, wherein the second opposing side is configured to be disposed near a tongue of the user during use, and wherein the oral hygiene device further comprises a securing mechanism that extends from the second opposing side.

2. The device of claim 1, further comprising a stability member spanning the distance between the first and second opposing sides at distal ends of the first and second opposing sides, wherein the stability member defines an aperture that is disposed between the first and second opposing sides.

3. The device of claim 1, wherein the second opposing side is slanted with respect to the first opposing side.

4. The device of claim 1, further comprising a material spanning the distance between at least one of the corresponding notch pairs.

5. The device of claim 4, wherein the material is wound about the oral hygiene device and around the first and second opposing sides.

6. The device of claim 1, wherein the device is insertable within a mouth of the user and each corresponding notch pair is configured to correspond to dental anatomy of the user.

7. The device of claim 6, wherein corresponding notch pairs are positioned to substantially align with a space between neighboring teeth of the user.

8. The device of claim 1, wherein the body is insertable within a user's mouth and each corresponding notch pair is configured to correspond to dental anatomy of the user.

9. An oral hygiene device comprising:
    a body having a first side and a second side, the first side and the second side defining a distance therebetween;
    a plurality of corresponding notch pairs, wherein each corresponding notch pair has a first notch positioned in the first side and a second notch positioned in the second side;
    an aperture in the body between the first and second sides; and
    a securing mechanism that extends from the oral hygiene device and that is configured to secure a flossing material to the oral hygiene device.

10. The device of claim 9, the body further comprising a stability member spanning the distance between the first and second sides at distal ends of the first and second sides.

11. The device of claim 9, further comprising the flossing material spanning the distance between at least one of the corresponding notch pairs.

12. The device of claim 11, wherein the securing mechanism extends from a portion of the device that is configured to be closer to a tongue of a user than to an inner cheek of the user when the device is disposed within a mouth of the user.

13. The device of claim 11, wherein the flossing material is wound about the body.

14. The device of claim 9, further comprising a gripping portion extending from the body, wherein the gripping portion further comprises an opening therein.

15. The device of claim 14, wherein the opening opens to an exterior surface of the gripping portion and is configured to receive a material therein.

16. A method of cleaning teeth comprising:
   providing an oral hygiene device having a body with opposing sides, the opposing sides defining a gap therebetween;
   positioning a material on the body to span the gap at a plurality of locations along the body;
   securing a portion of the material to a securing mechanism that extends from, and at, a distal end of the oral hygiene device;
   placing the device into a user's mouth; and
   applying the material concurrently into spaces defined between the user's teeth.

17. The method of claim 16, wherein the positioning a material on the body further comprises wrapping the material about the body.

18. A method of manufacturing the oral hygiene device of claim 1 comprising:
   making impressions of a user's teeth;
   creating a model of the user's teeth from the impressions;
   designing the oral hygiene device from the model, the oral hygiene device having a securing mechanism that extends from a distal portion of the oral hygiene device; and
   making the oral hygiene device.

19. The method of claim 18, wherein the making the device further comprises 3-D printing the device.

20. The method of claim 19, further comprising shipping by mail the impressions and the oral hygiene device from and to the user, respectively.

* * * * *